(12) United States Patent
Draper

(10) Patent No.: US 11,364,143 B2
(45) Date of Patent: Jun. 21, 2022

(54) NASAL MUCOSA HEATING AND OCCLUSION EYEWEAR

(71) Applicant: Lonnie Draper, Tallahassee, FL (US)

(72) Inventor: Lonnie Draper, Tallahassee, FL (US)

( * ) Notice: Subject to any disclaimer, the term of this patent is extended or adjusted under 35 U.S.C. 154(b) by 667 days.

(21) Appl. No.: 16/398,601

(22) Filed: Apr. 30, 2019

(65) Prior Publication Data

US 2019/0328575 A1    Oct. 31, 2019

Related U.S. Application Data

(60) Provisional application No. 62/664,342, filed on Apr. 30, 2018.

(51) Int. Cl.
*A61F 7/00* (2006.01)
*A61M 15/08* (2006.01)

(52) U.S. Cl.
CPC .......... *A61F 7/007* (2013.01); *A61M 15/08* (2013.01); *A61F 2007/0006* (2013.01); *A61M 2205/05* (2013.01)

(58) Field of Classification Search
CPC .......... A61M 15/08; A61M 15/085; A61M 16/0666; A61M 16/0672; A61M 16/0677; A61M 16/0683; A61M 16/0688; A61M 16/0694; A61M 2025/0226; A61M 2210/0618; A62B 23/06; A62B 18/082
See application file for complete search history.

(56) References Cited

U.S. PATENT DOCUMENTS

| | | | |
|---|---|---|---|
| 2,221,972 A | 11/1940 | Jones et al. | |
| 2,468,383 A * | 4/1949 | Tiffany | A61M 16/107 128/206.13 |
| 4,559,941 A * | 12/1985 | Timmons | A61M 16/0672 D16/322 |
| 4,708,446 A * | 11/1987 | Timmons | A61F 9/029 351/158 |
| 4,858,476 A * | 8/1989 | Tobin | G02C 11/00 351/158 |
| 5,193,534 A * | 3/1993 | Peppler | A61M 16/0666 128/207.18 |
| 5,363,153 A * | 11/1994 | Bailiff | G02C 11/00 351/158 |
| 6,772,762 B2 * | 8/2004 | Piesinger | A62B 7/00 128/857 |
| 6,886,562 B2 * | 5/2005 | Ishizuka | A61M 16/0666 128/206.18 |
| 7,981,097 B2 | 7/2011 | Paoli, Jr. | |

(Continued)

FOREIGN PATENT DOCUMENTS

| | | |
|---|---|---|
| CN | 104857648 | 8/2015 |
| WO | WO2010126554 | 11/2010 |
| WO | WO2016011423 | 1/2016 |

*Primary Examiner* — Dung T Ulsh
(74) *Attorney, Agent, or Firm* — McHale & Slavin, P.A.

(57) ABSTRACT

The instant invention provides an eyewear piece having a nasal mucosa heating and occlusion apparatus. The eyewear piece includes a bridge extending substantially across the wearer's face and having flexible joints at opposite ends thereof to attach temples, which extends over the ears to keep the eyewear on the wearer's face. The bridge includes a housing and depending therefrom is a nasal frame having nasal passageways to provide heat into the nasal cavity. It is contemplated that other therapeutic remedies are offered to the wearer.

24 Claims, 6 Drawing Sheets

(56) References Cited

U.S. PATENT DOCUMENTS

Figure 1:
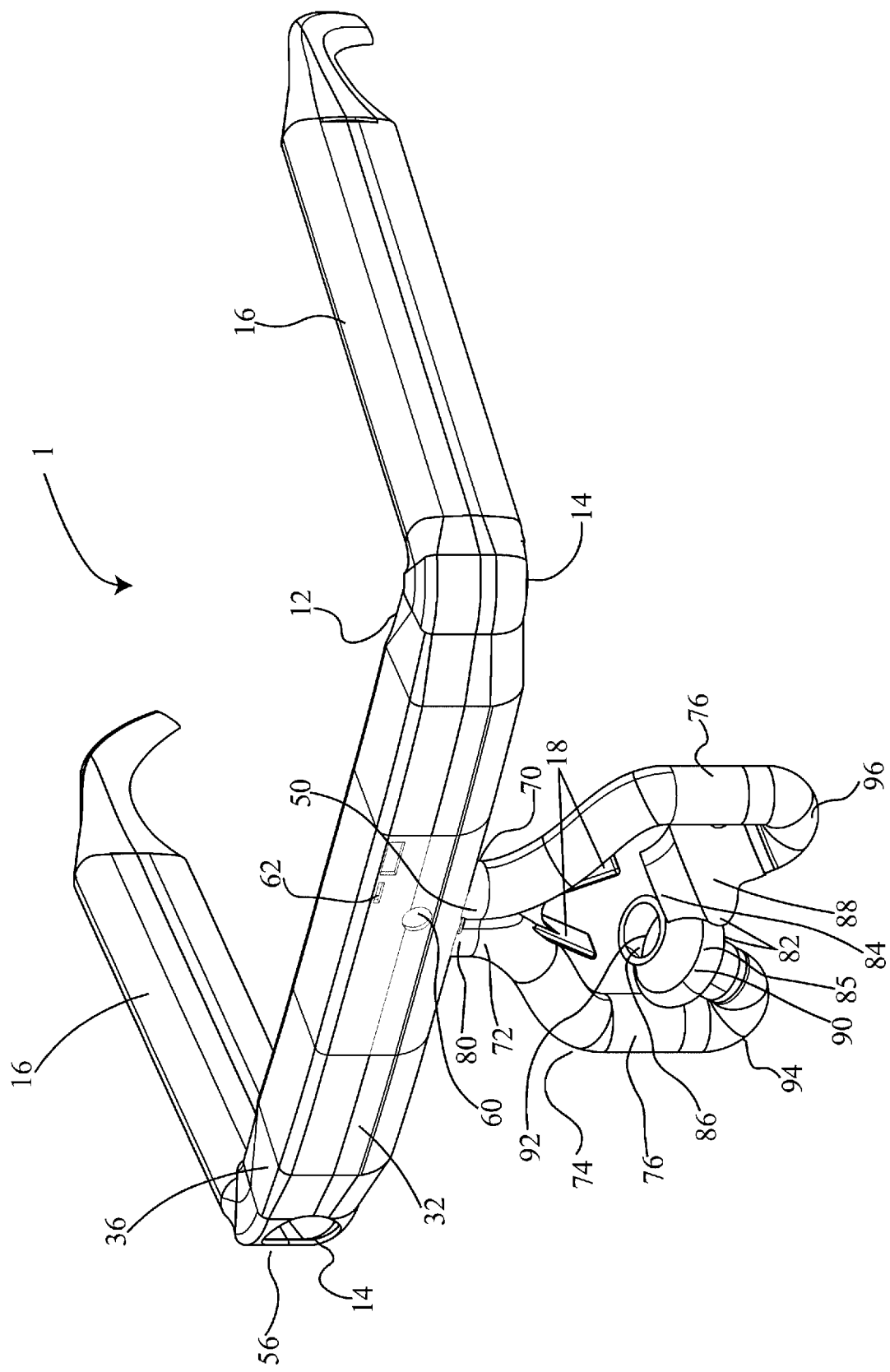
Figure 2:
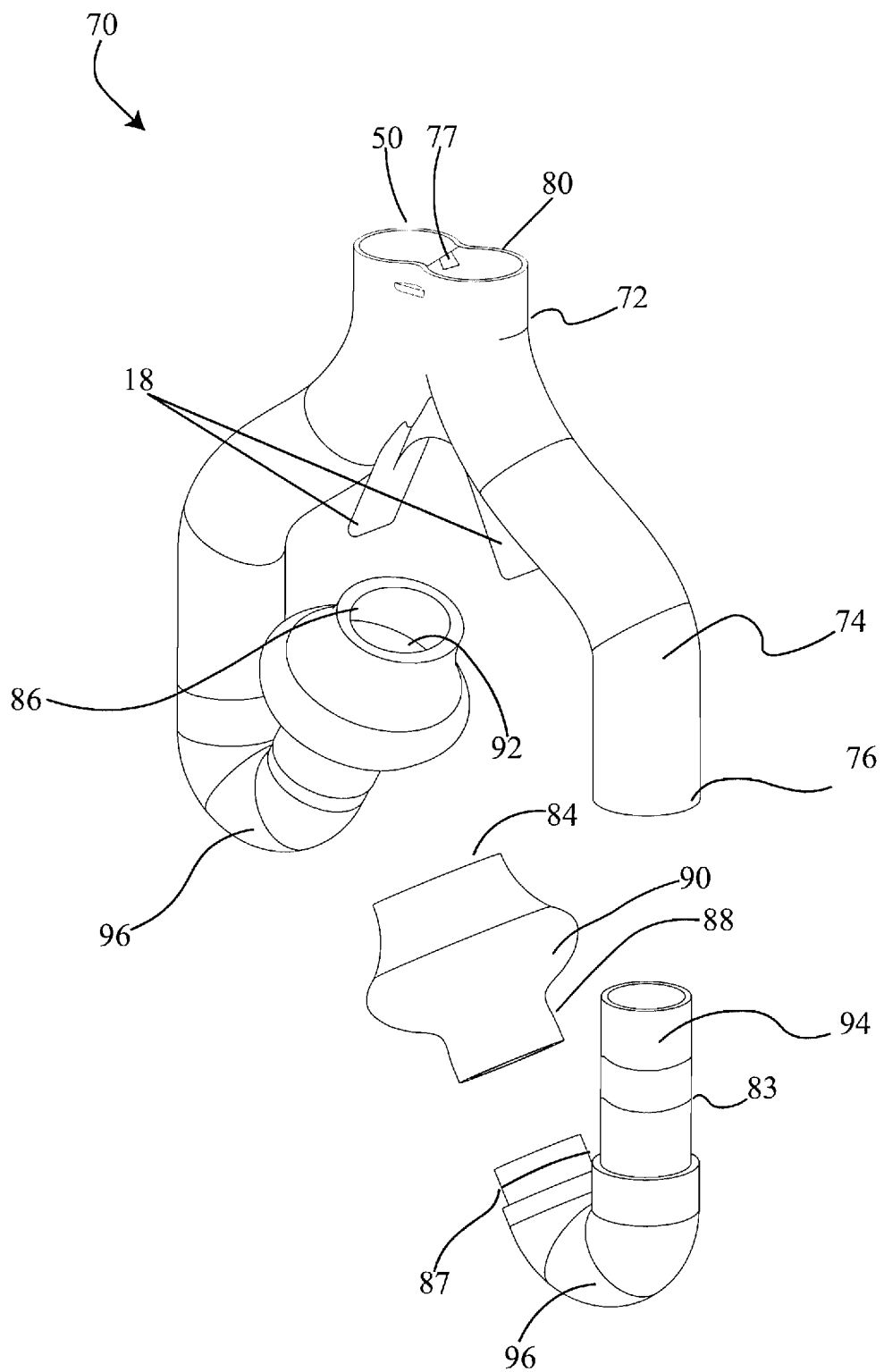

| | | | |
|---|---|---|---|
| 2004/0074500 A1* | 4/2004 | DePuy | A61M 16/0666 351/83 |
| 2009/0247967 A1* | 10/2009 | Delli Paoli, Jr. | A61M 11/044 604/521 |
| 2013/0056010 A1* | 3/2013 | Walker | A61M 16/204 128/202.16 |
| 2018/0125700 A1* | 5/2018 | Ray | A61M 16/024 |
| 2018/0200544 A1* | 7/2018 | Liu | A62B 7/10 |

\* cited by examiner

NASAL MUCOSA HEATING AND OCCLUSION EYEWEAR

PRIORITY CLAIM

In accordance with 37 C.F.R. § 1.76, a claim of priority is included in an Application Data Sheet filed concurrently herewith. Accordingly, the present invention claims priority to U.S. Provisional Patent Application No. 62/664,342, entitled "NASAL MUCOSA HEATING AND OCCLUSION EYEWARE", filed Apr. 30, 2018. The contents of which the above referenced application is incorporated herein by reference.

FIELD OF THE INVENTION

The present invention generally relates to eyewear, and more particularly, to eyewear having a nasal mucosa heating and occlusion apparatus.

BACKGROUND OF THE INVENTION

The term "nasal cavity" refers to each of the two sides of the nose or to the two sides combined. The nasal cavities condition the air that is to be received by the other areas of the respiratory tract. The air passing through the nasal cavity is warmed or cooled to within one degree of body temperature. In addition, the air is humidified and particulate matter, such as dust, is removed by vibrissae, short, thick hairs present in the vestibule. In the process of warming and humidifying the inhaled air, the nasal mucosa cools below normal body temperature. The entire mucosa of the nasal fossae is covered by a blanket of mucus, which lies superficial to the microscopic cilia and adheres to particulate matter, thereby removing it from the inhaled air. The nasal mucous membrane lines the nasal cavities, and is intimately adherent to the periosteum or perichondrium of the nasal conchae. It is continuous with the skin through the nares, and with the mucous membrane of the nasal part of the pharynx through the choanae. It is one of the most commonly infected tissues in adults and children. Inflammation of this tissue may cause significant impairment of daily activities, with symptoms such as stuffy nose, headache, mouth breathing, etc.

The common cold is a viral infectious disease of the upper respiratory tract that primarily affects the nose. This type of virus is specifically reproduced in the nasal mucosa at temperatures below the normal body temperature. The common cold does not usually cause complications, but can lead to days off work or school due to discomfort, which is caused by the symptoms. The diagnosis is based on symptoms, and the treatments are mainly symptomatic. Symptoms include runny or stuffy nose, sore throat, sneeze, cough, congestion, low grade fever, mild headache, increase appetite, feeling unwell, feeling chilled, headaches, muscle aches and pains, and thin or thick clear, yellow and/or green nasal discharge. Signs and symptoms may begin less than two days following exposure. Many signs and symptoms are caused by congestion from swelling of membranes and thickened mucus inside the nose. Laboratory evidence suggests that the cold virus may be sensitive to heat. Thus, devices that generate heat to the nasal cavity have been suggested for years to cure the common cold.

Devices for respiratory protection are prevalent in the prior art. U.S. Pat. No. 2,468,383 provides a mask type device with a nasal covering means to provide heated air into the nostril from the exhaled breath of the user. Unfortunately, this does not provide a sustained and prolonged amount of heated air sufficient to kill off the common cold. U.S. Pat. No. 2,221,972 describes a handheld air heating device that includes nasal airway passages for providing hot air into the nostrils. Such a device would be improved if it were attached to headwear so as to not inconvenience the cold sufferer by having to hold the device the entire time. U.S. Pat. No. 5,363,153 shows a heated nose pad attached to eyewear, specifically on top of the nose, not into the nostrils, that includes a powering means that is attached along the temple of the eyewear. This device heats from the outside of the nasal cavity and not into the nasal cavity, thus providing less effective means to combat the common cold.

U.S. Pat. Nos. 4,559,941 and 4,708,446 describe eyewear frames and nasal cannula assemblies to administer oxygen and other gases into the nostrils of the user. These eyewear devices provide eyewear having nasal cannula assemblies to provide oxygen from a remote oxygen tank. These devices are generally intended to supply high concentration oxygen for inhalation purposes in response to breathing in action by the user, and is not designed to provide a flow of hot air to the nasal mucosa. U.S. Pat. No. 5,193,534 provides eyewear having nasal airway passages attached, but the heated air draws its power remotely away from the eyewear and air from tubes that extend along the back of the eyewear to a respiratory tank or the like. U.S. Pat. No. 6,772,762 describes eyewear having nasal airway passages attached thereto, whereby heated air draws its power and air from tubes that extend along the back of the user and onto an attached belt. U.S. Pat. No. 7,981,097 describes eyeglasses having nasal airway passages removably attached thereto or removably attached a nose pad, but heated air draws its power from outside the eyewear frame and from a belt or a separate vehicle not on the user, such as a respirator tank. These prior art devices provide heated air, but are not intended to preserve a temperature range for treatment of the nasal mucosa or the common cold. Additionally, these devices include hardware, such as the power source, heating element, or respirator tank, which are all external to the eyewear, thereby making the entire apparatus very cumbersome. It would be advantageous to provide an eyewear that provides nasal mucosa heating and occlusion having the heating element and power source attached thereto.

SUMMARY OF THE INVENTION

The instant invention provides an eyewear piece having a nasal mucosa heating and occlusion apparatus. The eyewear includes a nasal frame and a bridge, which extends substantially across the wearer's face and has flexible joints at opposite ends thereof to attach temples, which extend over the ears to keep the eyewear on the wearer's face. The bridge is defined by a housing for heating and occlusion components, and depending from the bridge is a nasal frame having nasal passageways to provide heat into the nasal cavity. It is contemplated that other therapeutic remedies are offered to the wearer.

Accordingly, it is an objective of the instant invention to impart warmth to the nasal and nasal pharyngeal mucosa of the user in order to facilitate the inhibition of infecting viruses that cause the common cold.

Still another objective of the instant invention is to facilitate the lymphatic drainage of the nasal mucosa, cause arterial vasoconstriction, and inhibit arterial and venous congestion.

Another objective of the instant invention is to establish comfort to the user by regulating temperature and airflow within the nasal cavity, specifically to provide a dry heat at a specific temperature and flow rate to reduce the reproduction of virus proteins and particles that invade the nasal and nasopharyngeal mucosa.

Yet another objective of the instant invention is to provide a heating element that sits at the entry of the nasal cavity.

Still another objective of the instant invention is to provide an occlusion apparatus that opens and closes a port at the nasal cavity entry to provide active pressurization in the nasal airway for the purposes of reducing venous congestion, and for the reduction and collection of nasal discharge and snot.

Another objective of the instant invention is to provide an air circulation pattern that maximizes heat transfer to the nasal cavity.

Yet another objective of the instant invention is to provide an air filter at the nasal pillow to reduce obstruction from particles, such as but not limited to nasal hair. The air filter is not intended to be a virus filter.

Still another objective of the instant invention is to provide nasal pillows that work independently of each other, whereby air pressure and temperature at each nasal pillow is controlled independently to supply more pressure or heat to one nostril or the other. Still another objective of the instant invention is to increase comfort of the nasal mucosa via facilitating the Draper-Valsalva maneuver.

Still another objective of the instant invention is to increase comfort to a user by applying heat to the forehead proximate to the frontal sinus and the nose bridge and the cheek proximate to the maxillary sinus.

Still another objective of the instant invention is to facilitate the introduction of a vapor of medication or a vapor of fragrance to induce comfort and pleasure via the nasal manifold to the nasal passages.

Still another objective of the instant invention is to collect nasal drainage as it is discharged from the nose.

Other objectives and advantages of this invention will become apparent from the following description taken in conjunction with any accompanying drawings wherein are set forth, by way of illustration and example, certain embodiments of this invention. Any drawings contained herein constitute a part of this specification and include exemplary embodiments of the present invention and illustrate various objects and features thereof.

BRIEF DESCRIPTION OF THE FIGURES

FIG. 1 is a perspective view of eyewear piece;

FIG. 2 is a perspective exploded view of the nasal frame of the eyewear piece;

FIG. 3 is an exploded view of the eyewear piece;

FIG. 4 is a perspective view of the bridge of the eyewear piece;

FIG. 5 is a side view of the occlusion system of the eyewear piece; and

FIG. 6 is a sectional view of the occlusion system of the eyewear piece.

DETAILED DESCRIPTION OF THE INVENTION

While the present invention is susceptible of embodiment in various forms, there is shown in the drawings and will hereinafter be described a presently preferred, albeit not limiting, embodiment with the understanding that the present disclosure is to be considered an exemplification of the present invention and is not intended to limit the invention to the specific embodiments illustrated.

Referring now to the Figures in general, the present invention relates to an eyewear piece 1 which includes a bridge 12 extending substantially across the wearer's face. As shown in FIG. 1, the bridge 12 includes flexible joints 14 at the opposite ends thereof to attach temples 16. The temples 16 are long arms on the ends of the bridge 12 that extend over the ears to keep the eyewear on the wearer's face. The flexible joints 14 on the ends of the bridge 12 are slightly flexible or adjustable, which allows the temples 16 to fold inward and also extend or retract to allow for sizing adjustments. The bridge 12 is defined by a housing 30 and depending therefrom is a nasal frame 70 having nasal pillows 82 to provide heat into the nasal cavity. Between the upper conductors 74 of the nasal frame 70 is a pair of nose pads 18, a plastic piece that helps keep the eyewear in the proper position on the wearer's face and is designed for comfort and a snug fit, as well as allowing room for adjustment.

As shown in FIGS. 1 and 2, the nasal frame 70 is ergonomically shaped to fit around the periphery of the wearer's nose and terminates near the nasal cavity. The entirety of the nasal frame 70 is in fluid communication. The nasal frame 70 begins as a transfer member 50, herein defined as an interior manifold. The nasal frame 70 is generally comprised of a one-way adjustable entry tube 80 that splits into a pair of upper conductors 74. The upper conductors 74 are provided with an interior ridge (not shown) for frictional articulation with the U-shaped passage elbows 94 which holds the nasal pillows 82. The nasal frame 70 is comprised of a crescent end 72, thereinbetween upper conductors 74, and a termination end 76. The crescent end 72 of the nasal frame 70 includes the adjustable entry tube 80 that telescopically adjusts vertically into the bridge 12 (not shown) to provide proper positioning of the nasal frame 70. The crescent end 72 of the nasal frame 70 also interiorly includes an adjustable left-right manifold baffle 77. Repositioning of the baffle 77 towards the left decreases the air flow to the left side of the manifold 50, which increases the flow to the right nostril, and visa-versa. The termination end 76 of the nasal frame 70 frictionally engages with the U-shaped passage elbows 94 to allow for a limited degree of movement (vertically and rotationally) to allow for flexibility and adjustability to any wearer. The U-shaped passage elbows 94 have a tubular shape that slides telescopically into the termination end 76 of the nasal frame 70 and includes ring ridges 83 that frictionally engage with the interior ridges (not shown) of the termination end 76 of the nasal frame 70. The termination ends 76 have an internal reverse ridge that facilitate the adjustment of the U-shaped passage elbows 94 to specific heights in their vertical adjustment and allow for rotational adjustment as well (not shown). Similarly, the U-shaped passage elbows 94 include a raised ring 87 that secures the nasal pillows 82 and allows for rotational adjustment of the nasal pillows 82 to align elliptical shape with the elliptical nasal of the nasal cavity. It is contemplated that accordion-like U-shaped passage elbows 94 would allow for proper adjustment as well as the ability to position and set at various locations.

The nasal pillows 82 are constructed with an enlarged flexible rim 85 for optimal fitting within the nasal cavity to occlude the nasal cavity, and to collect nasal discharge. The nasal pillows 82 are constructed of a circular or elliptical cross-section, whereby the top of the nasal pillow 84 and the bottom of the nasal pillow 88 have a smaller diameter than the middle flexible rim portion 85 of the nasal pillow.

Furthermore, the top of the nasal pillow 84 is open ended 86. It is contemplated that a filter 92 may be positioned at the enlarged flexible rim portion 85 of the pillow, between the bottom of the nasal pillow 88 and the open end 86 of the nasal pillow to filter air as it leaves the nasal pillow 82. The open end 86 of the nasal pillow allows fluids, such as heated air, ozone, fragrances, essential oils, or the like to pass therethrough and enter the nasal cavity. The bottom of the nasal pillow 88 fits over the U-shaped passage elbows 94. The open end 86 of the nasal pillow is to be in contact with the entryway of the nasal cavity. The enlarged flexible rim portion 85 helps to occlude the airway in the pressurization mode of operation. Alternative embodiments of the instant invention contemplate a nasal heater 90 at the bottom of the nasal pillow 88 that heats the entirety thereof to warm the entryway of the nasal cavity. Thereinbetween the crescent end 72 and the termination ends 76 of the nasal frame 70 are removably attached U-shaped passage elbows 94. The U-shaped passage elbows 94 are positioned between the nasal pillows 82 and the one-way adjustable entry tube 80 and transition the fluid within the nasal frame 70 from downward to upward and into the nasal cavity. The U-shaped passage elbows 94 also provide a trap 96 for any nasal discharge to collect. Nasal discharge can seep out of the nasal cavity, into the nasal pillows 82, and ultimately collect at the bottom of the trap 96 of the U-shaped passage elbows 94. It is contemplated that the U-shaped passage elbows 94 and nasal pillows 82 are removable to allow proper disposal and cleaning of any debris collected therein. The U-shaped passage elbows 94 adjust vertically by frictionally engaging the termination end 76 of the nasal frame 70, the ring ridge 83 frictionally engages the plurality of inverse ring ridges on the interior of the termination end 76 of the nasal frame 70, as discussed before and not shown, thereby fixing the vertical height at set intervals. Furthermore, the ridge rings 83 allow for full rotational adjustment of the U-shaped passage elbows 94 in the nasal frame 70.

Figure 3:
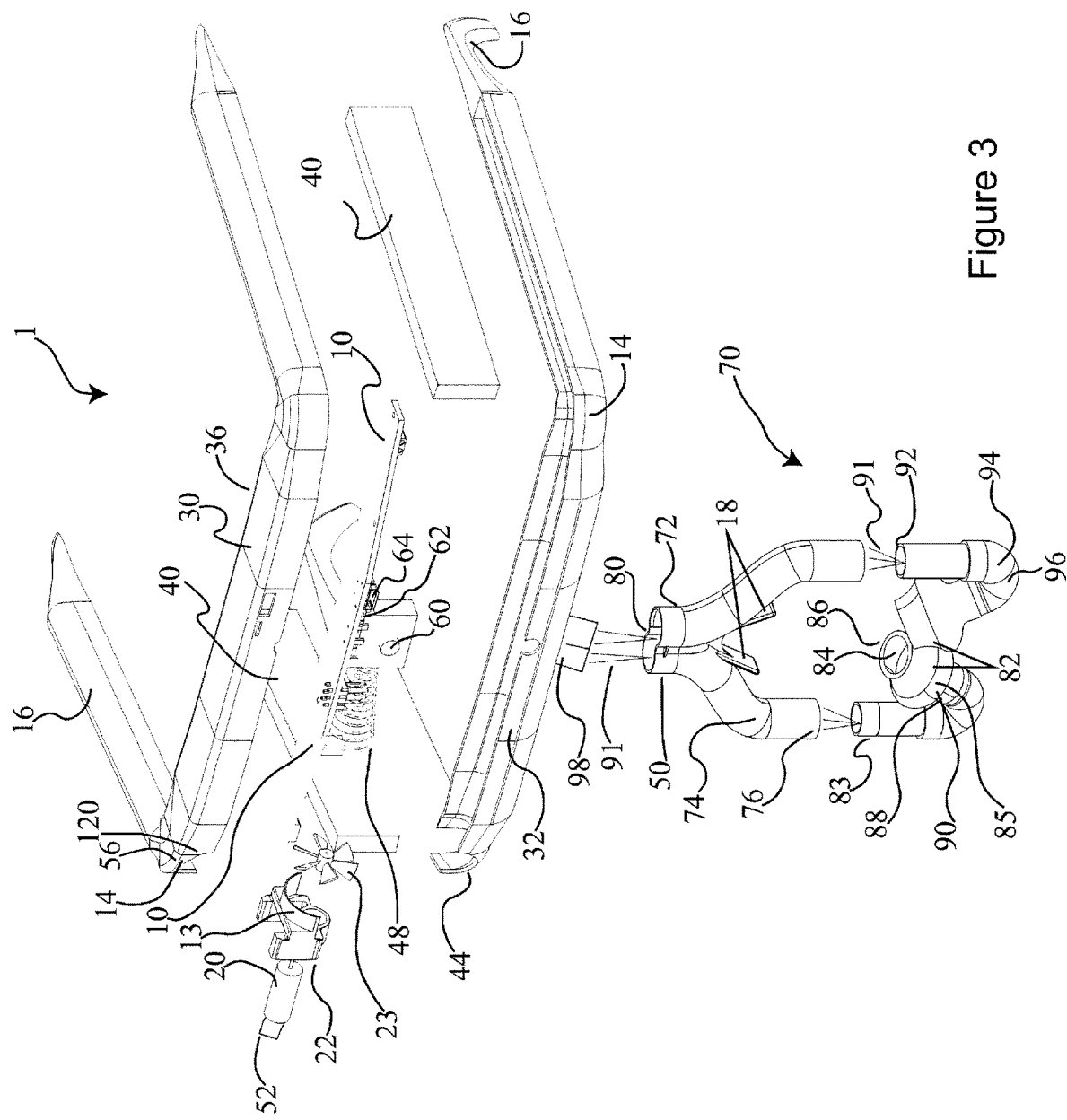
Figure 4:
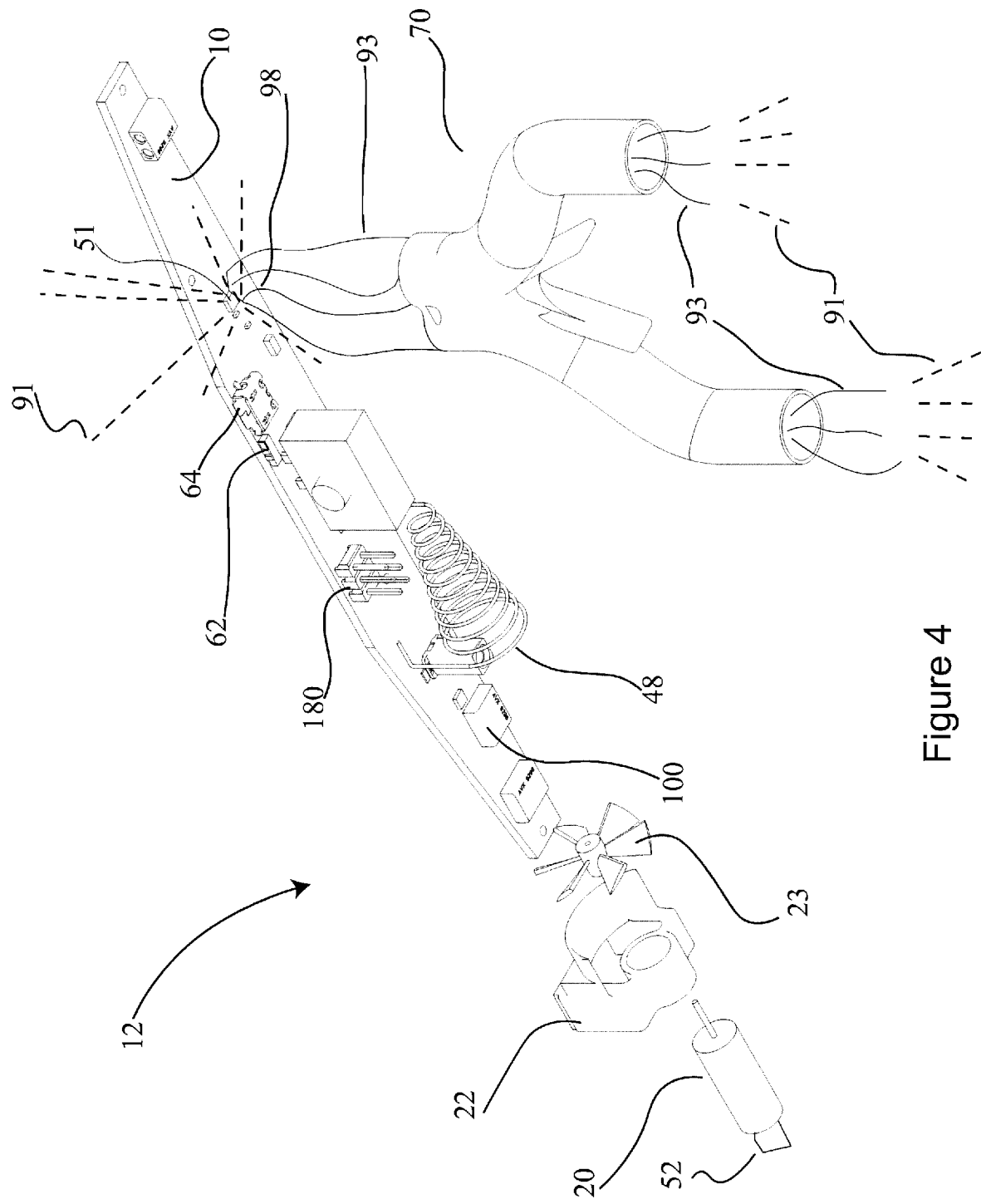

The bridge 12 and nasal frame 70 are in fluid communication, specifically from the air intake hole 44 and past the air baffle 51 which directs air to the bridge duct 98 where the air is directed into the transfer member or manifold 50 of the nasal frame 70, as seen in FIGS. 3 and 4. The bridge 12 houses various components within, specifically the circuit board assembly 10. The components housed within the bridge 12 are not limited to the positions suggested herein. Various accommodations and positions are contemplated. The bridge housing 30 has a quadrilateral shape and includes a front surface 32, back surface 34 (not shown), top portion 36, and bottom portion 38. A power source 40 is located within the housing 30 in the preferred embodiment the power source 40 is located within both temples 16, or in a singular temple 16. The power source 40 is electronically connected to all components that require such. Various power sources 40 are known to give off heat, thus it is contemplated that a small cooling hole (not shown) is positioned juxtaposed to the power source 40 to allow heat to escape from the power source. A plurality of nasal pillow heater wires 91 are electronically connected to the power source 40 and the nasal heater 90 on the nasal pillows 82 to provide warmth at the nasal cavity. As shown, the heater wires 91 pass through the bridge 12, into the manifold 50 at the nasal frame 70, split through the pair of upper conductors 74, and conclude at the enlarged flexible rim portion 85 of the nasal pillows 82. Also positioned on the housing 30 is an air intake hole 44. The air intake hole 44 allows air to pass from the ambient air and into the bridge 12. Various methods to drive air into the housing 30 are contemplated, such as a suction valve 46 electrically connected to the power source 40 that can drive air from the ambient space and into the housing 30. Another method is the pressure created by the wearer's breathing; by breathing inwardly, the user can also draw air from the ambient space and into the housing 30. Once the air is drawn into the housing 30 from the air intake hole 44, it is in fluid communication with the primary heater 48. The primary heater 48 warms the air to a specific temperature. FIGS. 3 and 4 shows details of the circuit board assembly 10 which holds the primary heater 48 which is electrically coupled to the various thermometers 180 which are monitored by a processor 100 to regulate the temperature with preprogrammed logic. The air temperature is regulated to produce optimum comfort and virus inhibiting activity. The thermally regulated air is passed through the manifold 50, which directs the heated air to the nasal pillows 82. Sequential thermometers 180 or other airflow sensing methodology are used to determine airflow velocity and are monitored by the processor 100 and regulated to produce optimum airflow for comfort and virus inhibiting activity.

Other components on the circuit card assembly 10 include the ON/OFF toggle switch 60 that is positioned and exposed on the front surface 32 of the housing 30. The switch 60 is exposed to allow the user to manually turn the apparatus ON and OFF. It is contemplated that the ON/OFF toggle switch 60 allows for vabiable setting to allow for various components to be turned ON and OFF or regulated to specific heat or flow levels. The ON/OFF toggle switch 60 also includes an LED indicator light 62 that is also exposed on the front surface 32 of the housing 30. The LED indicator light 62 informs the wearer that the apparatus has been turned ON or OFF and which program is operating as well as power source recharge level. It is contemplated that the LED indicator light 62 may include several LEDs, each of which may indicate the powering of various components.

Another component on the circuit board assembly 10 includes the processor 100. In order to control air temperature, air rate, ozone production rate, fragrance rate, medication administration, independent control of individual nasal pillows, or the like, the processor 100 is electronically connected to the sensors and active components. The processor 100 has programmed logic. A data and charging port 64 is electronically connected to all the components via the same processor 100. The data and charging port 64 is contemplated as a USB port, however, other means are contemplated. The charging port 64 allows the wearer to charge the power source 40 when not in use in order for the apparatus 1 to function properly when not being charged and while being charged. The data port 64 allows the wearer to control various aspects of the different components within the apparatus to program the processor 100 and to collect data.

As seen in FIG. 3, a motor 20 driven air pump fan blade 23, designed to be a ducted fan air pump, causes ambient air to be drawn into the intake hole 44 and pumped over the internal air heater 90 and out the manifold 50 to the nasal pillows 82. The motor mount 22 supports the motor 20. A metallic thermal shield 13 is positioned around the internal air heater 90 to protect the bridge housing 30 from heat. The metallic thermal shield 13 also acts as the duct for the ducted fan blade.

As shown in FIG. 4, positioned above the nasal frame 70 within the housing 30 is the manifold 50. The manifold 50 is fluidly connected to the primary heater 48. Air is pushed into the manifold 50 and then into the nasal frame 70 at the crescent end 72, whereby it then passes through the pair of nasal pillows 82. Positioned within the housing 30 is also an ozone production system 52. The ozone production system 52 is fluidly connected to the nasal frame 70 to force ozone into the nasal frame 70 for the treatment of air from contaminants and bacteria. The preferred embodiment contemplates the use of ultraviolet light to produce ozone. Ambient air is drawn in through the air intake hole 44 and drawn through the ozone production system 52 to produce ozone. Several ozone production systems can be used, such as but not limited to, UV ozone generators, vacuum-ultraviolet ozone generators, or the like. These systems employ a light source that generates a narrow ban of ultraviolet light in order to produce a small trace amount of ozone. The ultraviolet light can be directed through the nasal frame 70 or to the nasal pillows 82 via fiber optic light pipes 93 to clean the pillows during non-use. Furthermore, at least one of the temples 16 may contain a reservoir 54 that can hold fragrances, essential oils, or medication that can later be pumped through the nasal frame 70, specifically located in the occlusion system 56 in FIG. 6.

Figure 5:
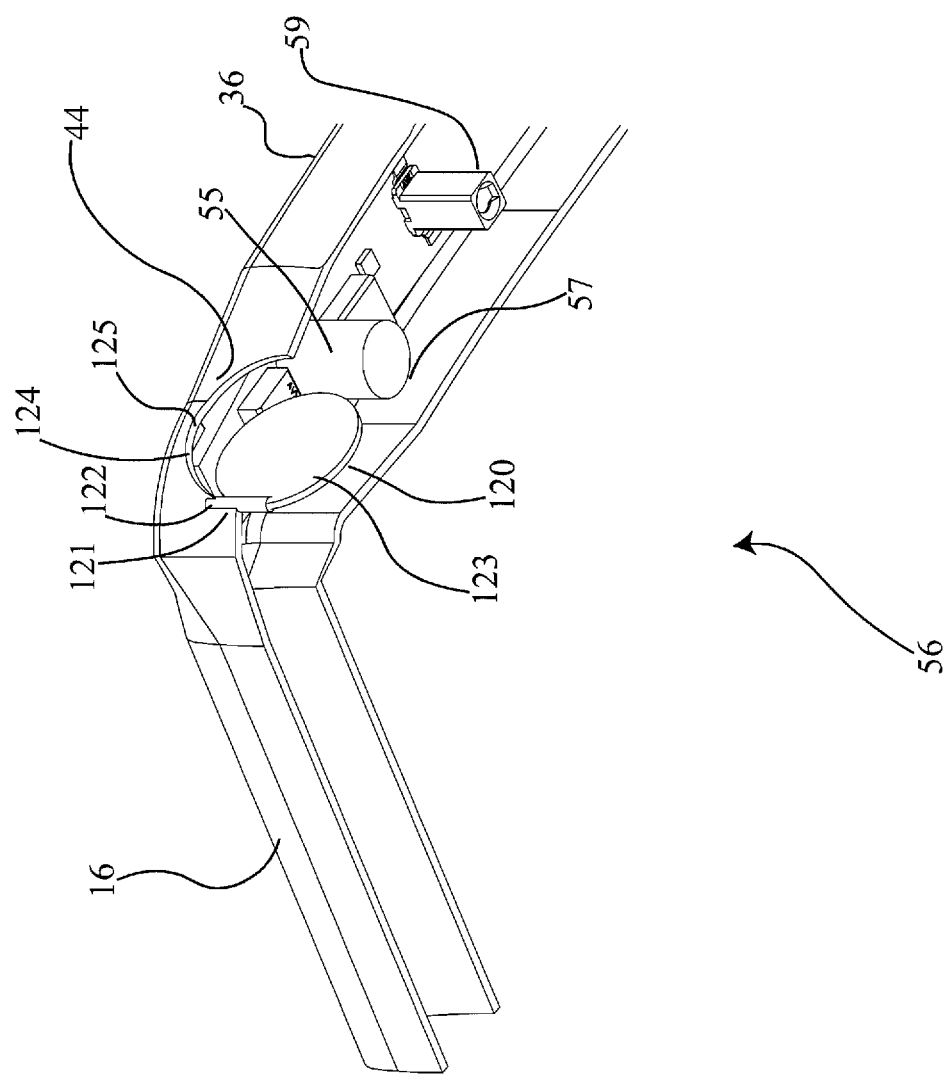
Figure 6:
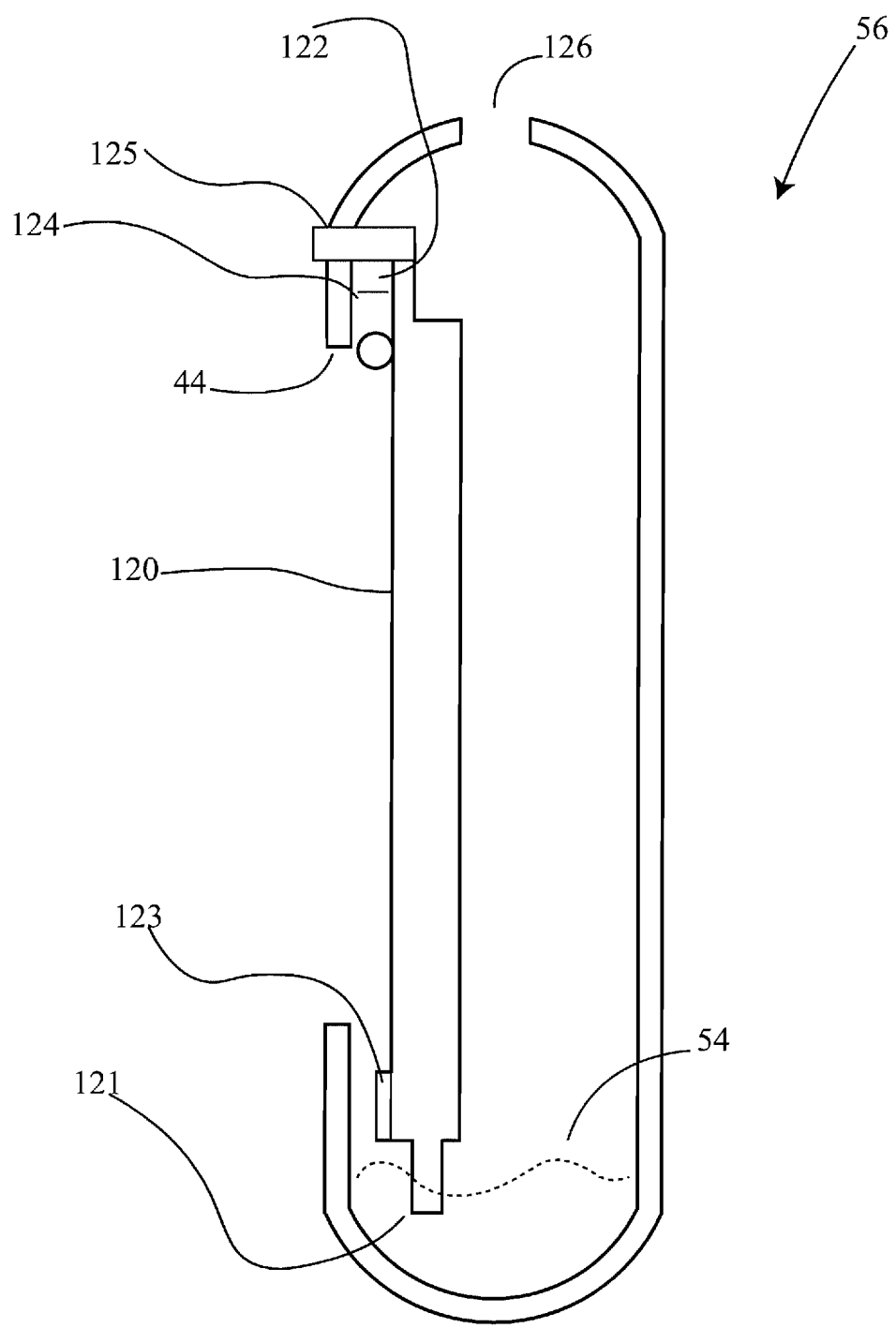

As shown in FIGS. 5 and 6, the eyewear piece 1 includes an occlusion system 56 to block air from exhalation from the nasal cavity for temporary relief of various ailments, such as nasal pressure, nasal congestion, or the like. The occlusion system 56 opens and closes a port pressurization gate 120 within the nasal frame 70 to provide active pressurization in the nasal airway for the purposes of reducing venous congestion, and for the reduction of nasal discharge and snot. The occlusion system 56 has a pressurization gate 120 located at the air intake hole 44. The pressurization gate 120 is located on a hinge 121 with a spring 122 on the opposing end to allow closure of the gate, passively preventing air from flowing in the opposite direction of usual design flow. A forced exhale in this state results in a "Valsalva Maneuver", which creates high pressure in the nasal airway and causes reduction of nasal congestion. The pressurization gate 120 has a seal 123 to reduce leakage when closed. The pressurization gate 120 has a latch 124 that intersects with the bridge housing 30 when the open button 125 is depressed. The pressurization gate 120 can be manually closed with the same open button 125, or can be set to passively close with the assistance of spring 122. FIG. 6 more aptly shows the closed state of the port pressurization gate 120, gate hinge 121, air intake hole 44, gate seal 123, gate latch 124, and the medication fill hole 126.

Additionally, as shown in FIG. 5, a medication container 55 can be positioned into the top portion 36 of the housing 30. The medication container 55 is in fluid communication with a medication dispenser 57 that allows the flow of medication at a regulated rate into the air stream within the nasal frame 70. Electronically coupled to the medication container 55 and dispenser 57 is a medication delivery sensor 59 that uses laser light diffraction or other methods to monitor and regulate the medication delivery.

All patents and publications mentioned in this specification are indicative of the levels of those skilled in the art to which the invention pertains. It is to be understood that while a certain form of the invention is illustrated, it is not to be limited to the specific form or arrangement herein described and shown. It will be apparent to those skilled in the art that various changes may be made without departing from the scope of the invention, and the invention is not to be considered limited to what is shown and described in the specification and any drawings/figures included herein.

One skilled in the art will readily appreciate that the present invention is well adapted to carry out the objectives and obtain the ends and advantages mentioned, as well as those inherent therein. The embodiments, methods, procedures and techniques described herein are presently representative of the preferred embodiments, are intended to be exemplary, and are not intended as limitations on the scope. Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:

1. A nasal mucosa heating and occlusion apparatus positionable on an individual's face, said apparatus comprising:
    an eyewear piece having a bridge constructed and arranged to extend substantially across the individual's face, said bridge includes flexible joints at opposite ends thereof and each terminating in attached temples, said temples extend over the individual's ear;
    a nasal frame depending from said bridge and in fluid communication therewith, said nasal frame having nasal pillows with an open end;
    a transfer member for introducing fluids selected from the group of: heated air, ozone, fragrances, and essential oils to pass through said open end of said nasal pillows and enter the individual's nasal cavity; and
    a power source mounted on said eyewear piece and electrically coupled to said transfer member.

2. The apparatus according to claim 1, wherein said nasal frame is ergonomically shaped to fit around the periphery of the individual's nose and terminating near a nasal cavity.

3. The apparatus according to claim 1, wherein said transfer member is defined as a manifold interiorly housed within said nasal frame.

4. The apparatus according to claim 3, wherein said nasal frame is comprised of a one-way adjustable entry tube that splits into a pair of upper conductors, each said upper conductor having frictional engagement with U-shaped passage elbows holding said nasal pillows.

5. The apparatus according to claim 4, wherein said nasal frame includes a crescent end between said upper conductors, crescent end includes said adjustable entry tube that telescopically adjusts vertically into said bridge for positioning of said nasal frame.

6. The apparatus according to claim 5, wherein said crescent end includes an adjustable manifold baffle, whereby positioning of said baffle decreases air flow to one side of said manifold which increases air flow to an opposite side of said manifold and thereby increase air flow through said one nasal pillow.

7. The apparatus according to claim 4, wherein said U-shaped passage elbows include a raised ring to secure said nasal pillows in position and allow for rotational adjustment of said nasal pillows to align with the elliptical shape of the nasal cavity.

8. The apparatus according to claim 1, wherein said nasal pillows are constructed with an enlarged flexible rim for optimal fitting within the nasal cavity to occlude the nasal cavity and to collect nasal discharge.

9. The apparatus according to claim 1, further including a nasal heater positioned at bottom of said nasal pillows, said nasal heater warms an entryway of the nasal cavity.

10. The apparatus according to claim 1, wherein said eyewear piece includes a processor electrically coupled to said power source to control said transfer member for introducing said fluids, including medication administration and independent control of said individual nasal pillows.

11. The apparatus according to claim 1, wherein said transfer member is further defined as a motor driven air pump for drawing ambient air into an intake hole and pumped over a nasal heater to said nasal pillows.

12. The apparatus according to claim 1, including an occlusion system to block air from exhalation from a nasal cavity, wherein occlusion system opens and closes a port pressurization gate within said nasal frame to provide active pressurization in a nasal airway.

13. The apparatus according to claim 12, wherein said pressurization gate is located on a hinge with a spring on an opposing end to allow closure of said gate and passively preventing air from flowing in an opposite direction.

14. The apparatus according to claim 1, wherein said transfer member is further defined as a medication dispenser that allows medication at a regulated rate into an air stream within said nasal frame, said medication dispenser including a laser light diffraction sensor to regulate medication delivery.

15. A nasal mucosa heating and occlusion apparatus positionable on an individual's face, said apparatus comprising:
    an eyewear piece having a bridge constructed and arranged to extend substantially across the individual's face, said bridge includes flexible joints at opposite ends thereof and each terminating in attached temples, said temples extend over the individual's ear;
    a nasal frame depending from said bridge and in fluid communication therewith, said nasal frame having nasal pillows with an open end including a one-way adjustable entry tube that splits into a pair of upper conductors, each said upper conductor having frictional engagement with U-shaped passage elbows holding said nasal pillows, a crescent end between said upper conductors wherein said adjustable entry tube telescopically adjusts vertically into said bridge for positioning of said nasal frame;
    a manifold interiorly housed within said nasal frame for introducing fluids selected from the group of: heated air, ozone, fragrances, and essential oils to pass through said open end of said nasal pillows and enter the individual's nasal cavity; and
    a power source mounted on said eyewear piece and electrically coupled to a transfer member;
    whereby positioning of a baffle decreases air flow to one side of said manifold increases air flow to an opposite side of said manifold to increase air flow through one said nasal pillow of said nasal pillows.

16. The apparatus according to claim 15, wherein said nasal frame is ergonomically shaped to fit around the periphery of the individual's nose and terminating near the nasal cavity.

17. The apparatus according to claim 15, wherein said U-shaped passage elbows include a raised ring to secure said nasal pillows in position and allow for rotational adjustment of said nasal pillows to align with the elliptical shape of the nasal cavity.

18. The apparatus according to claim 15, wherein said nasal pillows are constructed with an enlarged flexible rim for optimal fitting within the nasal cavity to occlude the nasal cavity and to collect nasal discharge.

19. The apparatus according to claim 15, further including a nasal heater positioned at bottom of said nasal pillows, said nasal heater warms an entryway of the nasal cavity.

20. The apparatus according to claim 15, wherein said eyewear piece includes a processor electrically coupled to said power source to control said transfer member for introducing said fluids, including medication administration, and independent control of said individual nasal pillows.

21. The apparatus according to claim 15, wherein said transfer member is further defined as a motor driven air pump for drawing ambient air into an intake hole and pumped over an air heater to said nasal pillows.

22. The apparatus according to claim 15, including an occlusion system to block air from exhalation from the nasal cavity, wherein said occlusion system opens and closes a port pressurization gate within said nasal frame to provide active pressurization in a nasal airway.

23. The apparatus according to claim 22, wherein said pressurization gate is located on a hinge with a spring on an opposing end to allow closure of said gate and passively preventing air from flowing in an opposite direction.

24. The apparatus according to claim 15, wherein said transfer member is further defined as a medication dispenser that allows medication at a regulated rate into an air stream within said nasal frame, said medication dispenser including a laser light diffraction sensor to regulate medication delivery.

* * * * *